United States Patent [19]
Corey

[11] Patent Number: 5,803,063
[45] Date of Patent: Sep. 8, 1998

[54] TELEPHONE MEDICAMENT DELIVERY DEVICE

[76] Inventor: Craig Corey, 18801 River Falls Dr., Davidson, N.C. 28036

[21] Appl. No.: 806,927

[22] Filed: Feb. 26, 1997

[51] Int. Cl.⁶ .......................... A61M 15/00; A61M 16/10; A61M 11/00
[52] U.S. Cl. ............................... 128/203.12; 128/200.14; 128/200.18
[58] Field of Search ........................ 128/200.14, 200.24, 128/202.27, 203.12, 203.14, 202.13, 202.15, 202.16, 204.18, 205.22, 205.25, 207.14, 200.18, 200.21

[56] References Cited

U.S. PATENT DOCUMENTS

| | | |
|---|---|---|
| 2,840,649 | 6/1958 | Hodges ............................... 128/200.14 |
| 3,316,907 | 5/1967 | Goupil . |
| 4,454,877 | 6/1984 | Miller et al. . |
| 4,593,688 | 6/1986 | Payton ................................ 128/204.18 |
| 4,669,461 | 6/1987 | Battaglia et al. . |

Primary Examiner—Kimberly L. Asher
Attorney, Agent, or Firm—Bell Seltzer Intellectual Law Firm of Alston & Bird, LLP

[57] ABSTRACT

There is provided a device to augment the delivery of medication to a patient in aerosolized or gaseous form. The device includes a means, such as a nebulizer, for supplying medication coupled to the mouthpiece of a telephone-shaped handle. The telephone-shaped handle has a gripping portion, an earpiece at one end and a mouthpiece at the other end. The earpiece may include means to generate music or the like. The delivery device is especially useful for use with small children and infants.

5 Claims, 2 Drawing Sheets

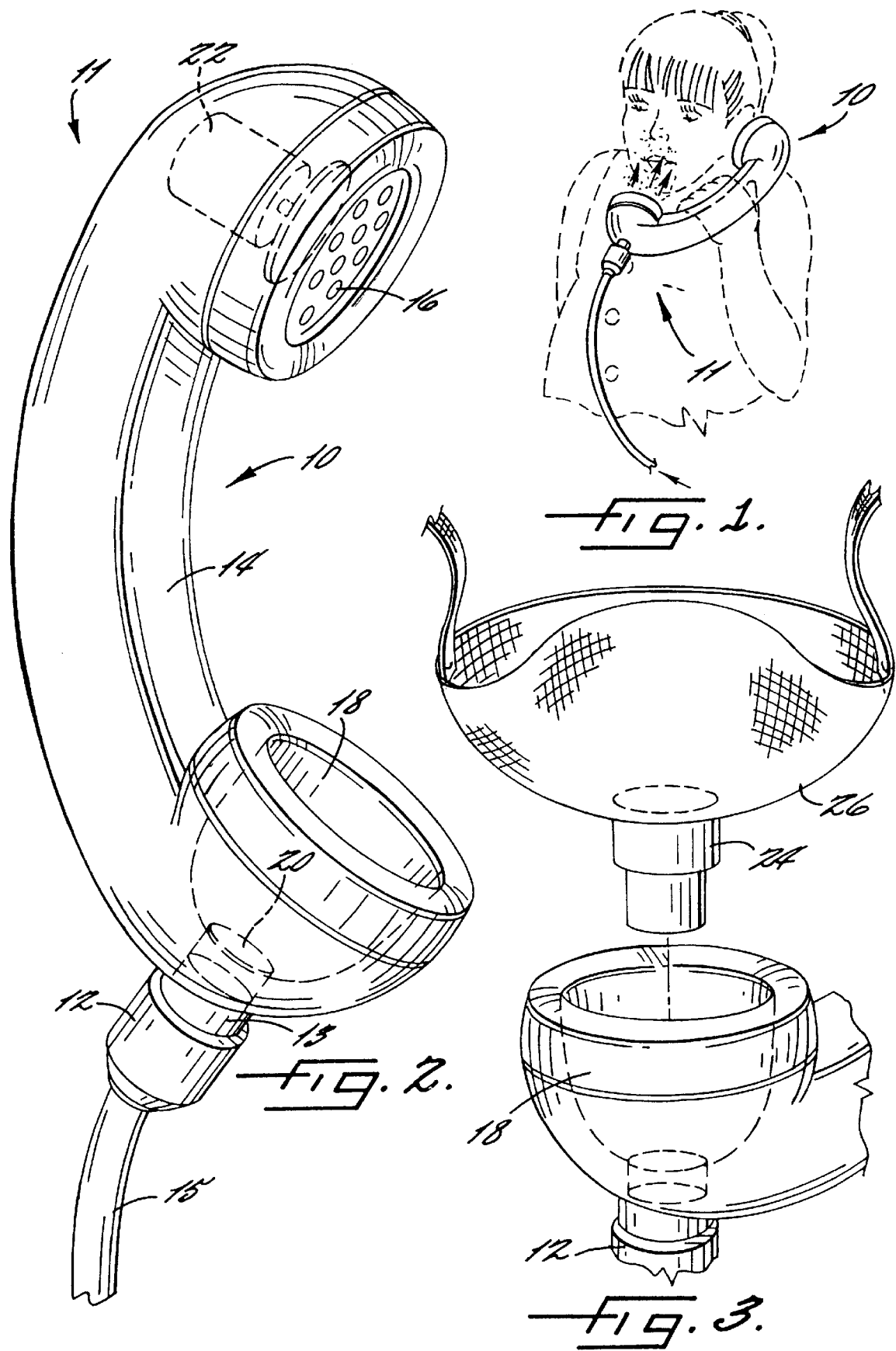

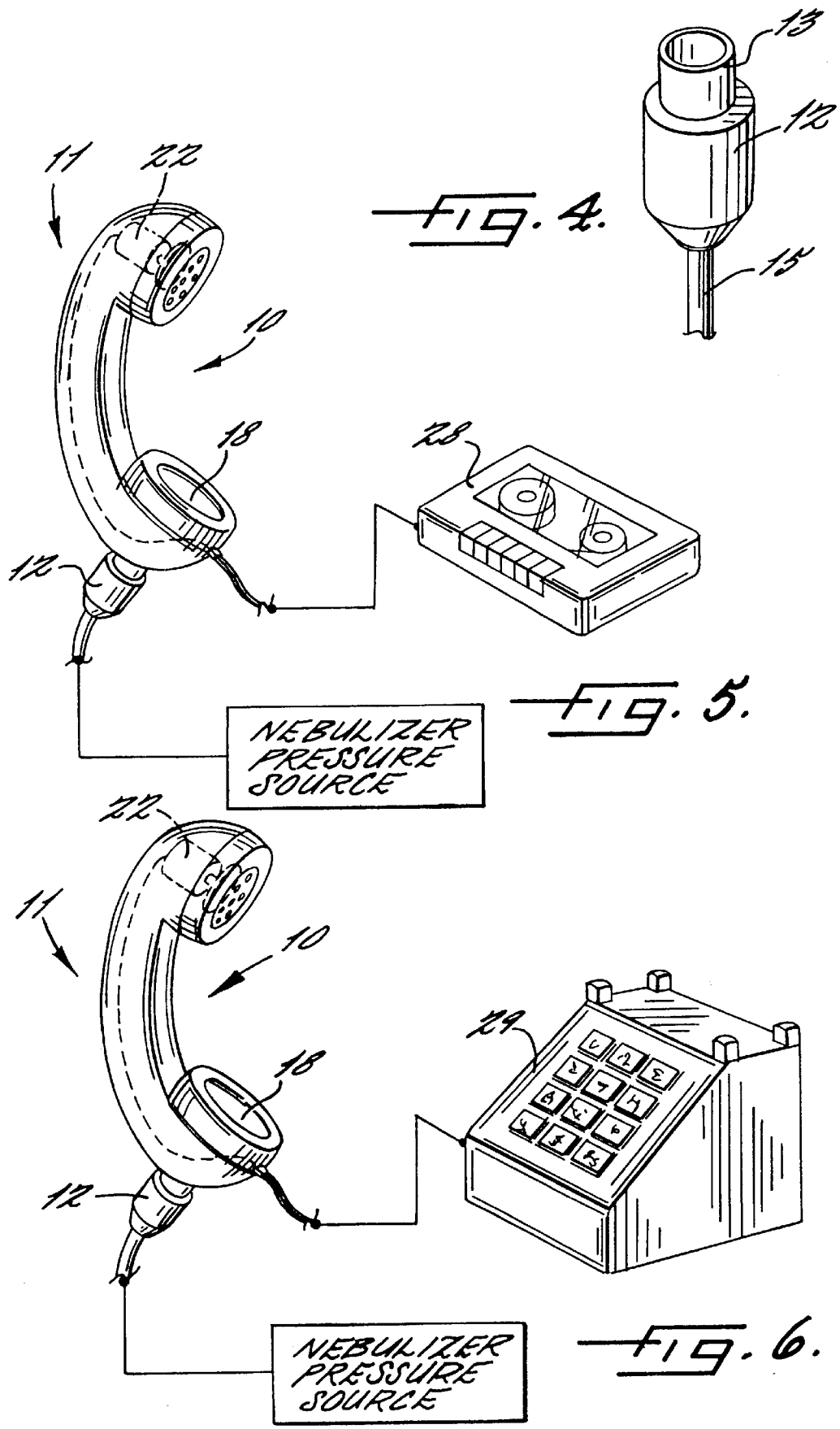

ously,063

TELEPHONE MEDICAMENT DELIVERY DEVICE

BACKGROUND OF THE INVENTION

The present invention relates to a device to augment the delivery of medication. More particularly, the present invention relates to a hand held device to augment the delivery of medication in aerosolized or gaseous form.

Millions of patients worldwide are affected with acute and chronic respiratory diseases, such as asthma, croup, cystic fibrosis (CF), respiratory syncytial virus (RSV), pneumonia, bronchopulmonary dysplasia (BPD) and bronchitis. These respiratory diseases frequently require a regular program of medication which is often given on a daily basis in aerosolized form. Medications frequently utilized in the treatment of asthma include bronchodilators, such as albuterol and anti-inflammatory agents, such as cromolyn sodium and leukotriene inhibitors. Antibiotics, such as pentamidine, are nebulized in the treatment of AIDS pneumonia. Medications used in the treatment of CF may be nebulized. In addition, there is sometimes the need to provide oxygen to a patient. Although treatment for certain respiratory diseases is practiced on a regular basis there are often unexpected attacks among both older and younger patients.

Respiratory attacks provide particular anxiety when they occur in infants or small children below the age of six or so. The presently used delivery devices often require a mask to be placed over or held in close proximity to the child's face to be effective. These small children are quite frequently anxious and uncooperative at the time the medication is needed due to their illness and unfamiliar surroundings. The presently used medication delivery devices tend to increase the anxiety, crying and combative behavior of the child. This not only makes the delivery of the medication difficult, it stresses the parents and care givers.

There is a need for a user-friendly device to augment the delivery of medication for supplying a medication in aerosolized or gaseous form which is attractive, simple and effective in the treatment of infants and small children with respiratory diseases.

SUMMARY OF THE INVENTION

It is an object of the present invention to provide a device to augment the aerosolized delivery of medication to a patient.

Another object of the present invention is to provide a hand held device to augment the delivery of medication in aerosolized or gaseous form to an infant or small child.

The present invention provides a device to augment the delivery of medication, such as asthma drugs, antibiotics, surfactant, oxygen or the like in aerosolized or gaseous form to a patient. The delivery device includes a means for supplying medication in combination with a telephone-shaped handle having a gripping portion and an earpiece at one end of the gripping portion and a telephone mouthpiece at the other end of the gripping portion. The mouthpiece is attached to the means for providing medication. The medication supply means is preferably a conventional nebulizer. The telephone mouthpiece has therein a receptacle, for example, a 17 mm opening, designed to accept a conventional nebulizer unit without adaptation. Other nebulizer units may have slightly variable sizes unique to their products. The insertion opening in the mouthpiece may be of flexible material which would allow for some variation in size of the nebulizer insertion stem. The nebulizer may be attached by inserting the stem of the nebulizer unit into the receptacle opening of the mouthpiece, which is held in place by friction or other means.

In a preferred embodiment of the invention, the earpiece of the handle includes a musical device which plays while the patient is receiving medication and results in a soothing effect. In yet another embodiment, there is provided an extender for use with a mask. This extender fits into the bowl of the mouthpiece portion of the device. A mask may then be attached to provide for higher oxygen concentrations if necessary.

The aerosolized medicine flows freely to the a patient's mouth and nose through the open mouthpiece. The medication delivery device is especially useful for treating small children and infants.

BRIEF DESCRIPTION OF THE DRAWINGS

Other objects, features and advantages of this invention will be apparent from the following detailed description taken in conjunction with the drawings in which:

FIG. 1 is an environmental view of a small child using the medication delivery device of the present invention;

FIG. 2 is a perspective view of a preferred embodiment of the medication delivery device of the present invention illustrating the musical device in the earpiece;

FIG. 3 is a partial view of another embodiment of the delivery device of the present invention showing the use of a mask attached to the extender inserted into the handle mouthpiece;

FIG. 4 is a detail of a nebulizer unit showing the stem for insertion into the device;

FIG. 5 shows another embodiment of the medication delivery device of the present invention designed for long-term use, being attached to a source of music; and FIG. 6 shows yet another embodiment of the medication delivery device of the present invention.

DETAILED DESCRIPTION OF THE PREFERRED EMBODIMENTS

The present invention will now be described more fully hereinafter with reference to the accompanying drawings, in which a preferred embodiment of the invention is shown. This invention may, however, be embodied in many different forms and should not be construed as limited to the embodiments set forth herein; rather, this embodiment is provided so that this disclosure will be thorough and complete and will fully convey the scope of the invention to those skilled in the art.

Referring now to FIG. 1, there is shown an environmental view of a small child using the medication delivery device 10 of the present invention. As shown more clearly in FIG. 2, there is provided a delivery device 10 for supplying medication to a patient. The delivery device 10 includes a means 12, such as a nebulizer, for supplying medication in aerosolized or gaseous form. As used herein the term medication includes, where applicable, oxygen. The medication supply means 12 is combined with a telephone-shaped handle 11 having a gripping portion 14, an earpiece 16 at one end of the gripping portion 14 and a mouthpiece 18 at the other end of the gripping portion 14.

The mouthpiece 18 of telephone-shaped handle 11 is attached to the means for supplying medication 12. The medication supply means 12 may be a conventional nebulizer having a medication supply inlet which is attached to a supply line 15 from a nebulizer pressure source and an outlet, such as an ACORN nebulizer from Nellcor Puritan Bennett. The external mouthpiece receptacle 20 is an opening of variable size designed to accept existing nebulizer units without adaptation. The attachment of the medication supply means 12 to the external receptacle 20 of the mouthpiece 18 is accomplished by inserting the stem 13 of the nebulizer unit 12 into the external receptacle hole 20. The device will enhance the delivery of medication because the telephone is a play toy to every child. It is a familiar object generally associated with the child's regular environment. It is not a threatening, unknown object thrust over the child's mouth.

Optionally, the earpiece 16 of the telephone-shaped handle 11 may include a means 22 to generate music or the like. The means 22 may be a computer chip having prerecorded music or a story such as those found in, for example, greeting cards or a speaker attached to an external source. In this embodiment the music means 22 will further enhance the child's comfort with the situation ensuring appropriate delivery of needed medications and easing the stress for all involved.

As shown in FIG. 1 the dimensions of the telephone-shaped handle 11 are appropriate to fit a child's smaller ear to mouth distance. With placement of the telephone to the child's ear, the mouth of the nebulizer to the child's mouth and nose occurs without further maneuvers. The telephone-shaped handle may be made of plastic, and stay with the child during his or her stay in the office, emergency room or the like. The aerosolized medicine flows freely to the child's facial area through the open mouthpiece 18. This version of the invention is cleanable to allow for reuse by the same patient.

In another embodiment, that shown in FIG. 3, there is provided a mouthpiece 18 having an extender 24 for use with a mask 26. The extender 24 extends through the opening in mouthpiece 18 to connect the mouth of nebulizer 12 with the mask 26. The receptacle on the base of the mouthpiece is the insertion point for the nebulizing device. In this embodiment, a simple adaptor will allow an oxygen mask to be placed in the mouthpiece to fit over the face if required, still delivering the needed medication or oxygen with the benefit of the phone.

The above-described device to augment delivery of mediation to small children may be produced so as to be disposable, especially desirable with devices used in hospitals, clinics, offices or ambulances for limited use and subsequent disposal. However, it is also desirable that the delivery devices of this invention may be produced for multiple-use application, particularly at home, where the handle 11 would be made of injection molded plastics suitable for home sterilization.

In FIG. 4, there is shown, in greater detail, the nebulizer 12 with extender 13. The nebulizer is attached to a medication supply tube 15. As shown in FIG. 3, the nebulizer 12 fits in a tight-fit through the speaker handle 18 or it may be fixably attached through an opening in the handle.

In FIG. 5, there is shown another embodiment of the medication delivery device 10 of the present invention which is particularly useful for home or extended use. As shown in FIG. 5, an audio system 28 is attached to the mouthpiece 18 of the telephone-shaped handle 11 and the parents or care givers can play age-appropriate tapes of music, songs or stories to calm the child while the medication is being delivered.

Also there is shown another embodiment of the present invention in FIG. 6 in which the medication delivery device 10 is shown connected to a play console 29 (which looks like a telephone with different buttons making different sounds, songs, stories or the like).

In the drawings and the specification, there has been set forth a preferred embodiment of the invention and, although specific terms are employed, the terms are used in a generic and descriptive sense only and not for purpose of limitation, the scope of the invention being set forth in the following claims.

That which is claimed is:

1. A medication delivery device adapted for use by a patient comprising:

a telephone-shaped handle having a gripping portion, an earpiece at one end of said gripping portion and a mouthpiece at the other end of said gripping portion; and means for augmenting delivery of medication in aerosolized or gaseous form, said means having a medication supply inlet and a medication supply outlet, said means for augmenting the delivery of medication being attached to said mouthpiece receptacle so that when said delivery device is used, said medication is delivered through said mouthpiece.

2. The device according to claim 1 wherein said means for delivering said medication is attached to a nebulizer or oxygen source.

3. The device according to claim 1 wherein said earpiece includes a device for providing music.

4. The device according to claim 1 wherein said handle is plastic.

5. A medication delivery device adapted for use by a patient comprising:

a telephone-shaped handle having a gripping portion, an earpiece at one end of said gripping portion and a mouthpiece at the other end of said gripping portion; and means for augmenting delivery of medication in aerosolized or gaseous form, said means having a medication supply inlet and a medication supply outlet, said means for augmenting the delivery of medication being attached to said mouthpiece receptacle so that when said delivery device is used, said medication is delivered through said mouthpiece, said means for delivering said medication includes an adapter allowing attachment of a mask to the mouthpiece of the telephone-shaped handle, enabling said mask to fit over the patient's face.

* * * * *